United States Patent [19]

Hsu et al.

[11] Patent Number: 4,575,562

[45] Date of Patent: Mar. 11, 1986

[54] DIMETHYL ADIPATE FROM BUTADIENE

[75] Inventors: Charles K. Hsu, Pensacola; Frank Dobinson, Gulf Breeze, both of Fla.

[73] Assignee: Monsanto Company, St. Louis, Mo.

[21] Appl. No.: 652,049

[22] Filed: Sep. 19, 1984

[51] Int. Cl.[4] .............................................. C07C 67/38
[52] U.S. Cl. .................................... 560/204; 560/183; 560/207; 562/590; 568/673
[58] Field of Search ................. 560/204; 502/152, 155, 502/162, 166, 171; 562/590

[56] References Cited

U.S. PATENT DOCUMENTS 4,169,956 10/1979 Kummer et al. ..................... 560/204
4,171,450 10/1979 Kesling et al. ....................... 560/204
4,171,451 10/1979 Kummer et al. ..................... 560/204

*Primary Examiner*—Natalie Trousof
*Assistant Examiner*—Vera C. Clarke
*Attorney, Agent, or Firm*—Thomas N. Wallin

[57] ABSTRACT

Dimethyl adipate is produced from dimethyl hex-3-enedioate which is prepared by carbonylation of butadiene under reactive conditions in the presence of an alcohol, a platinum-group-metal catalyst and quinone oxidant.

19 Claims, No Drawings

DIMETHYL ADIPATE FROM BUTADIENE

FIELD OF THE INVENTION

A. Background

Adipic acid is conventionally made by the catalyzed nitric-acid oxidation of cyclohexanol or cyclohexanone or mixtures, the alcohol or ketone or mixtures being made by air oxidation of cyclohexane or by hydrogenation of phenol.

As the relative cost of phenol or benzene-derived cyclohexane increases with respect to linear hydrocarbons, it becomes important to seek ways to make industrially important adipic acid from other feedstocks. This invention is concerned with a process for making dimethyl adipate by carbonylation of butadiene.

B. The Prior Art

Catalyzed carbonylation of hydrocarbons to give monocarboxylated and/or dicarboxylated products is well known.

Tsuji reported the carbonylation of complexes of palladium chloride and olefins to give $\beta$-chloroacyl chlorides (J. Amer. Chem. Soc., 86, 4851-3, 1964) which could be esterified to give the corresponding $\beta$-chloro-esters. Fenton disclosed the oxidative carbonylation of hydrocarbon olefins in the presence of an alcohol and a soluble salt of a multivalent metal with an oxidation potential greater than the platinum-group-metal catalyst also present (U.S. Pat. Nos. 3,397,225 and 3,397,226), forming esters of unsaturated acids. Thus the reaction of carbon monoxide with ethylene in the presence of palladium chloride yielded methyl methacrylate in good selectivities. When the $Cu^{++}/Cu^{+}$ couple was used, high conversions were obtained, since the cupric ion maintains palladium in its $Pd^{++}$ form; air or oxygen bubbled through the reactants converted cuprous ion to cupric ion, thus maintaining the redox cycle. Cupric ion used to oxidize Pd to $Pd^{2+}$ may also be kept in the $Cu^{2+}$ state by anodic oxidation (Fenton, U.S. Pat. No. 3,481,845).

In U.S. Pat. No. 3,755,421 (Fenton et al), quinones or hydroquinones of benzene or naphthalene are used as redox agents in the carbonylation or discarbonylation of hydrocarbon olefins containing only one double bond, such as ethylene. A Group VIII nobel metal compound is used, where the metal ion is in an elevated oxidation state. Oxygen or air is used to regenerate the quinone from the hydroquinone in this redox reaction. The patent also states that a suitable dehydrating agent may be beneficial in the carbonylation process. Among those dehydrating agents mentioned are acetals and ketals—including 1,1-dimethoxycyclohexane, derived from methanol and cyclohexanone—and orthoesters such as methyl orthoformate.

Palladium-catalyzed carbonylation of 1,3-butadiene in an alcohol solvent was described by Tsuji in 1971 (S. Hosaka and J. Tsuji, Tetrahedron, 27, 3821-29, 1971). Using ethanol as solvent and palladium acetate as catalyst, a 97.8% selectivity to ethyl 3-pentenoate was obtained at 16% conversion of the butadiene. No di-ester was produced. At higher conversions (36.5%) using the same catalyst, 8.6% of di-esters were formed, together with only 47.4% of ethyl 3-pentenoate and about 43% of branched or saturated monocarboxylic esters.

Japanese Kokai No. 75,130,714 (Teijin, Ltd.) describes the formation of esters by carbonylating a conjugated diene in the presence of monohydric alcohols, molecular oxygen and a suitable redox salt. Thus butadiene in methanol containing palladium chloride and cupric chloride under carbon monoxide and oxygen pressure gave 10 molar % yield of methyl 2,4-pentadieneoate, 25 molar % yield of a mixture of methyl 2-pentenoate and methyl 3-pentenoate, and only about 2.5 molar % yield of dimethyl hex-3-enedioate. Only the last named product is a dicarbonylated product.

Kesling and Zehner (U.S. Pat. No. 4,166,913) describe the catalytic oxidative carbonylation of conjugated dienes in the presence of a salt of a platinum-group metal, an iron or copper "oxidant salt" compound such as cupric chloride, plus equimolar amounts of an alcohol and an enol ether such as methyl vinyl ether or a cyclic ketal such as 1-methoxycyclohexene. In U.S. Pat. No. 4,171,450, essentially the same art is taught, but instead of the equimolar mixture of alcohol and enol ether or alkoxycycloalkene, the use is taught of two molar equivalents (based on butadiene) of a dehydrating agent such as 1,1-dimethoxycyclohexane and no more than catalytic quantities of an alcohol. The 1,1-dimethoxycyclohexane clearly serves to provide the hydrocarbyl (in this case, methyl) radical of the ester products, being itself the diketal formed from methanol and cyclohexanone by removal of water. In both cases, butadiene reacts with carbon monoxide, and oxygen that is also present re-oxidizes the iron or copper "oxidant salt".

In U.S. Pat. No. 3,509,209, Fenton teaches the carbonylation of butadiene in the presence of a palladium-containing catalyst and an aqueous hydrohalic acid (hydrochloric or hydrobromic). In one example, about 2M% of adipic acid was isolated, based on butadiene charged to the reactor. In another example, a 9.2 molar % yield of pentenoic acid was obtained. Another example showed the carbonylation of 2-pentenoic acid, under the same general conditions to yield 55 molar % of adipic acid.

The two-step carbonylation of butadiene to methyl pentenoate followed by further carbonylation to dimethyl adipate is known (e.g., U.S. Pat. Nos. 4,169,956 and 4,171,451 to BASF). The patents show the use of a cobalt carbonyl catalyst. The first step appears to be slow and to require high pressures (e.g. about 9000 psig). These constraints would tend to make such a process much less economical than one based on a faster process carried out at significantly lower pressures.

SUMMARY OF THE INVENTION

This invention describes the preparation of dimethyl adipate from 1,3-butadiene via dimethyl hex-3-enedioate.

The dimethyl hex-3-enedioate is produced by reacting 1,3-butadiene with carbon monoxide at elevated temperatures and pressures, in the presence of methanol, and a catalytic amount of both a platinum-group metal compound in its high oxidation state and an organic oxidant such as a quinone. The term "platinum-group metal" is used to refer to the elements ruthenium, rhodium, palladium, osmium, iridium and platinum. The alcohol is employed in a quantity that is at least stoichiometric, based on the dicarboxylic ester to be formed. Optionally, dehydrating materials such as ketals, acetals, orthoesters or metaboric acid or esters may be included. The platinum-group metal compound may optionally contain ligands. Oxygen used to regenerate the quinone oxidant may be added along with the carbon monoxide, in an alternating manner with the carbon monoxide, or in a separate vessel.

The reaction may be carried out in a single reactor or, where it is desired to keep the oxygen and carbon monoxide separated for safety reasons, for example, in multiple vessels. The reaction may be run in a batch, continuous, or semi-continuous mode. By semi-continuous is meant a system where reactants are continuously fed to a reactor but no reaction products are drawn from the reactors until the cycle is completed.

The methanol is employed in this invention at a level of at least 2 moles per mole of diester to be produced.

Dehydrating agents which may optionally be added in small amounts to the reaction mixture, and which serve only to maintain desirable anhydrous conditions, include compounds such as methyl orthoformate, metaboric acid, 2,2-dimethoxypropane, 1,1-dimethoxycyclohexane, methyl vinyl ether, 1-ethoxy-cyclohexene, etc.

The catalysts of this invention are compounds of the platinum-group elements, also referred to as Group VIII elements but excluding iron, cobalt and nickel. They comprise the elements ruthenium, rhodium, palladium, osmium, iridium and platinum. Compounds of palladium are preferred. Mixtures may be used. Examples of suitable compounds are ruthenium trichloride, rhodium tribromide, palladium iodide, osmium sulfate, iridium nitrate and platinum chloride. Metals or oxides may be used directly when conditions are such that a suitable catalytic salt is formed during the reaction.

The catalyst is preferably combined with a suitable ligand such as a trialkyl or triaryl phosphine, or the corresponding compounds of arsenic and antimony; nitriles; phosphites; alkali-metal halides, etc. Examples include triphenyl phosphine, tris(p-methoxyphenyl)-phosphine, tris(p-chlorophenyl)phosphine, tributyl phosphine, triphenyl arsine, triethyl arsine, triphenyl stibine, benzonitrile, acetonitrile, propionitrile, valeronitrile, succinonitrile, glutaronitrile, triphenyl phosphite, lithium chloride, sodium bromide, lithium iodide, potassium iodide, copper chloride, etc.

The catalyst-ligand complex may be prepared outside the reaction vessel or, preferably, may be formed in situ by adding the ligand and the platinum-group metal compound separately. The ligand compound may be employed in more than stoichiometric quantities if desired; if desired, it may be used as part or all the solvent for the reaction.

The catalyst may be homogeneous or heterogeneous. In the heterogeneous form it may be present as a slurry or impregnated on silica, alumina, carbon, etc. or on natural or synthetic zeolites or other inert materials. The catalyst may also be in a polymer-bound form. The amount of catalyst, as platinum-group metal atomic equivalents per mole of diene can be 0.001 to 5 gm. atoms/100 gm. mole, preferably between 0.01 and 1.0 gm.atoms/100 mole.

Solvents for the carbonylation reaction of this invention include benzene, toluene, xylene, cyclohexane, cyclopentane, cyclooctane, n-hexane, iso-octane, 2,5-dimethylheptane, acetonitrile, propionitrile, benzonitrile, cyclohexanone, acetone, acetophenone, 2-butanone, 1,2-dimethoxyethane, 3,6,9-trioxaundecane, 2,5,8-trioxanonane, 2,2-diethoxypropane, 1,1-dimethoxycyclohexane, ethyl acetate, methyl propionate, butyl propionate, methyl benzoate, dimethyl adipate, etc.

Small amounts of acids like acetic, trifluoroacetic, sulfuric, hydrochloric, hydrobromic or hydroiodic acid may be added to the reaction mixture if desired.

The quinone additive used to maintain the platinum-group metal in its oxidized state may be 1,4-benzoquinone, 2,5-dichloro-1,4-benzoquinone, 2,6-dichloro-1,4-benzoquinone, tetrachloro-1,4-benzoquinone(p-chloranil), 2,3-dicyano-1,4-benzoquinone, 2,3-dichloro-1,4-naphthoquinone, tetramethyl-1,4-benzoquinone, 2,3-dichloro-5,6-dicyano-1,4-benzoquinone, 2,5-diphenyl-1,4-benzoquinone, 2,3-dimethyl-1,4-naphthoquinone, 1,4-napthoquinone, etc. The preferred internal oxidant is p-chloranil(tetrachloro-p-benzoquinone).

Optionally, the corresponding hydroquinone or quinone/hydroquinone mixtures may be used.

The quinone or hydroquinone may be adsorbed on an inert material such as natural or synthetic zeolites, zirconium phosphate, etc., or it may be combined as part of an organic polymer, as is described in an article in Chemical & Engineering News, page 11 of the Nov. 15, 1982 edition and also by J. Lieto and others in Chem-Tech, January 1983, pages 46–53.

Sufficient oxygen must be used in the reaction to maintain the quinone oxidizing additive at a concentration of quinone sufficient to maintain enough of the platinum-group metal complex in its higher oxidation state, i.e. in its catalytically active form for the carbonylation process of the instant invention. The oxygen may be added along with the carbon monoxide—care being taken to avoid formation of explosive mixtures of oxygen and carbon monoxide—or in a separate reaction vessel, or carbon monoxide and oxygen may be added in a suitable alternating fashion to the reaction.

The instant process does not produce water during the carbonylation step of the process. Oxidative regeneration of the quinone additive from its analogous hydroquinone does form water, however. If carbonylation and quinone-regeneration take place in the same vessel, addition of sufficient dehydrating agent is desirable to minimize side reactions which may include oxidation of the butadiene or its derivatives. If carbonylation and quinone-regeneration are carried out in separate vessels, the quinone-containing feed to the carbonylation reactor should be substantially anhydrous. This dehydration may be carried out using the same chemical dehydrating agents already mentioned, or by passing the quinone-containing feed through a suitable solid dehydrating medium, or by removing the water by distillation.

The carbonylation process may be carried out at total pressures (butadiene solvent and carbon monoxide) of 350 atmospheres or greater, more preferably at 121–350 atmospheres or greater.

The temperature of the carbonylation can be in the range 60°–190° C., preferably around 100° C.

DESCRIPTION OF THE PREFERRED EMBODIMENTS

In a preferred embodiment, the desired intermediate dimethyl hex-3-enedicate(DMH), $CH_3OOCCH_2CH=CHCH_2COOCH_3$, can be readily hydrogenated using known methods, to form dimethyl adipate (See U.S. Pat. No. 4,189,559 herewith incorporated by reference). This ester can be hydrolyzed by known methods, to yield adipic acid.

The following examples are meant to be illustrative of the instant invention and are not intended to be limiting. The reaction equipment and general reaction procedure and the analytic techniques employed are described first before exemplary details are provided.

The carbonylation reactions described in the examples below were carried out in a 300 cc corrosion-resistant Hastelloy C autoclave capable of withstanding pressures up to 3000 psig. The autoclave was equipped with an externally driven stirrer, means of heating and cooling, a pressure gauge, feed lines for butadiene vapor, carbon monoxide gas and nitrogen gas, a discharge valve for obtaining the product of the reaction, and a rupture disc added as a safety feature.

For the pressures of carbon monoxide required in the examples below, it was desirable to further compress carbon monoxide from a commercially supplied cylinder of the pure gas, by means of a compressor, into a 1000 cc autoclave.

A calculated and accurately weighed amount of palladium-group metal catalyst compound, hereinafter referred to as "catalyst", was charged to the 300 cc reactor along with the desired quantity of the required quinone oxidant compound ("quinone"), methanol as the esterification agent ROH, and a suitable solvent. The autoclave was then attached to the autoclave head and stirring means, and the heating means was attached. The autoclave was pressurized to 1400 psig (94 atm) with nitrogen to check the system for leaks. If satisfactory, the reactor was then charged with butadiene that had been preweighed in a small stainless steel cylinder; transfer of the butadiene was achieved by applying a nitrogen pressure of about 40 psig (2.7 atm).

The autoclave was then heated to about 60° C., then the stirring means was started and set at about 2500 rpm. The speed of the stirrer is not critical, and only sufficient agitation is needed to maintain the reactor contents well-mixed and any insoluble additives in a good suspension in the reaction medium.

Carbon monoxide was charged into the autoclave until the pressure gauge attached thereto read a pressure 200–400 lbs. (13–27 atm) lower than the finally desired pressure. The heating means was switched on and set to allow the reaction to achieve the desired temperature. At this time, additional carbon monoxide was allowed to enter the reactor until the desired pressure was achieved.

As the reaction proceeded more carbon monoxide was added to maintain the pressure at the desired level. Reactions were stopped after two to six hours by cooling the reaction mixture to about 60° C., switching off the stirring means and releasing the remaining pressure by venting the pressured gases into an off-gas collector. This off-gas collector was equipped with electrical heating tape, a pressure gauge and valves to which could be attached sampling cylinders that could then be used in various analytical procedures.

The reaction autoclave was purged with additional nitrogen until the gauge pressure on the off-gas collector read 20–40 psig.

The off-gas was equilibrated for about 3 hours by heating one side of the collector, using a heat lamp.

The liquid reaction product was drained from the 500 cc reaction autoclave into a 500 cc sample bottle. The autoclave was rinsed with methanol, and these washings were collected separately. The following analyses were performed:

| SAMPLE | ANALYZED FOR: |
| --- | --- |
| Liquid product mixture | Unreacted butadiene and mono- and dicarbomethoxylated products, etc. |
| Reactor methanolic wash | Unreacted butadiene and mono- and dicarbomethoxylated products, etc. |
| Off-gas | Butadiene carbon dioxide, carbon monoxide. |

All three samples from each example were anlyzed by gas-liquid-partition chromatography (GLPC), using either a 5'6"×0.125" stainless steel column or a 6'×0.125" stainless steel column, both packed with Chromosorb GHP beads surface-coated with 5 wt. % SP-1000. Chromosorb GHP (a tradename of Johns-Manville Company) is a specially purified diatomaceous earth rendered inert by silation with dimethyl-dichlorosilane and sized, in this case to between 60 and 80 mesh. SP-1000 is a poly(ethylene glycol) of average molecular weight 20,000, the terminal hydroxyl groups having been esterfied with a derivative of terephthalic acid. It is manufactured by Supelco, Bellefonte, Pa. The chromatography equipment was temperature-programmed from 75° C. to 230° C. at 8°/minute to provide analyses of the crude reaction product and the reactor methanolic wash. On reaching 230° C., the temperature was maintained there for an additional 10 minutes. The carrier gas used in the GPLC analyses was helium at 78 psig (6.2 atm), flowing at 50–60 cc/minute.

The monocarbonylated products were quantified by integration of the GLPC trace of the corresponding peaks, relative to an internal standard (dimethyl glutarate).

The dicarbonylated product, dimethyl hex-3-enedioate (DMH) was independently synthesized and the known substance used to quantify the amount of this material in the GLPC traces of the reaction products. DMH exists in cis- and trans- forms, and the GLPC trace of the standard and reaction products showed a major peak with a "shoulder" indicating the presence of a second component.

The off-gases were analyzed in a related fashion, except that the GLPC column was maintained at a constant 25° C.

Mono- and di-carbonylated products produced by reaction of butadiene with carbon monoxide and the alcoholic reactant were further identified by the procedure known as GC/MS (Gas chromatography coupled with mass spectrometry). In GC/MS techniques, the components of a mixture are separated by GLPC and each separated fraction is subjected to mass spectrometric (MS) analysis. MS usually involves bombardment of the organic fractions with a beam of medium-energy electrons (50–100 electron volts). The technique is described on pp 340–345 of Basic Principles of Organic Chemistry by J. D. Roberts and Marjorie C. Caserio (W. A. Benjamin, Inc., Menlo Park, Calif.) Second Edition, 1977.

The liquid reaction products in the examples below are divided into monocarbonylated products and the dicarbonylated product, dimethyl hex-3-enedioate, the desired product (DMH). The monocarbonylated products comprised:

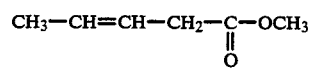

methyl 3-pentenoate (M3P);

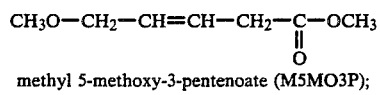

methyl 5-methoxy-3-pentenoate (M5MO3P);

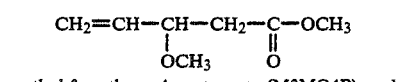

methyl 3-methoxy-4-pentenoate (M3MO4P); and

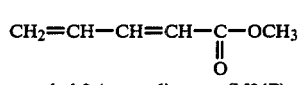

methyl 2,4-pentadienoate (M24P)

All these 4 monocarbonylation products are precursors to the desired product:

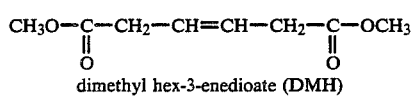

dimethyl hex-3-enedioate (DMH)

On occasions, small amounts of a reaction product of methanol and BD were found:

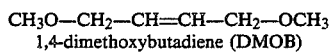

1,4-dimethoxybutadiene (DMOB)

This trace material, believed also to be a precursor to DMH, is classified as a "monocarbonylated product" in the tabular data for the examples.

EXAMPLE 1

Using the equipment, procedures and analytical techniques already described, the reaction autoclave was charged with:
Butadiene (8.8 g., 163 mmoles)
Methanol (15 cc, 328 mmoles, 2.01 moles/mole butadiene)
Sulfuric acid (0.507 g., 5.2 mmoles)
Palladium chloride (0.447 g., 3 mmoles)
Tetrachloro-p-benzoquinone (19.007 g., 79.2 mmoles)
Toluene (60 cc) and
Propionitrile (60 cc)

The reaction was carried out as described above, using a reaction temperature of 100° C. and a pressure of 1800 psig (121 atm). Products were analyzed using the techniques described above.

The product sample weighed 117.2 g. The reactor methanolic wash weighed 195.3 g. After GLPC, the various monocarbonylated products were shown to have been formed in the following amounts:
M3P—0.37 g. (3 mmoles)
M5MO3P—1.58 g. (14 mmoles)
M3MO4P—0.41 g. (3 mmoles)
M24P—1.34 g. (12 mmoles)

The desired product, DMH, weighed 4.65 g. (27 mmoles). The percentage molar selectivity (M% selectivity) to DMH was therefore:

$$\frac{27 \text{ mmoles}}{(27 + 3 + 14 + 3 + 12) \text{ mmoles}} = \frac{27}{52} = 45.8\%$$

Conversion of butadiene (hereinafter BD in these examples) was:

$$\frac{59 \text{ mmoles } BD - \text{derived products}}{163 \text{ mmoles } BD \text{ charged}} = 36.2\%$$

As a check on the experiment and analyses, the liquid product mixture, the reactor methanolic wash and the off-gases were analyzed by GLPC and the total weight of unreacted butadiene in these three mixtures was added to the weight converted, as calculated from the analytical results for mono- and dicarbonylated products. The off-gas calculations were corrected for standard temperature (298° K. or 25° C.) and pressure (14.7 psia, one atmosphere). Thus:

Liquid Product Mixture:
117.2 g. × 0.285% BD content × 0.011
calibration factor = 0.370 g. BD
Reactor Methanolic Wash:
195.3 g. × 0.043% BD content = 0.008 g.
Off-gas collector:
30 psig (2 atm), 50° C., 28 liter volume:
$$0.070\% \; BD \text{ content} \times 28 \times \frac{(30 + 14.7 \text{ psig } (2 + 1 \text{ atm}))}{(14.7 \text{ psig } (1 \text{ atm}))} \times$$

$$\frac{(273 + 25)}{(273 + 30)} = 5.49 \text{ g.}$$

Butadiene (molecular weight 54) converted, based on products:

$$59 \text{ mmoles} \times 54 = 3.19 \text{ g.}$$

Butadiene accountability is therefore the sum of butadiene accounted for in the products plus the measured BD that did not react divided by the amount of BD charged, all in grams:

$$\frac{0.370 + 0.008 + 5.49 + 3.19}{8.8} = 103\%$$

EXAMPLE 2

The charge to the autoclave consisted of:
BD—10 g. (185 mmoles)
Methanol—5 cc (109 mmoles, 0.59 moles/mole BD)
Sulfuric Acid—0.5 g. (5.1 mmoles)
Bis(triphenylphosphine)palladium chloride—2.2 g. (3.1 mmoles)
Tetrachloro-p-benzoquinone (TPB)—80.1 g. (333.8 mmoles)
Toluene—107.6 cc The reaction was carried out as in Example 1. The reaction temperature was 100° C., the pressure 1800 psig (121 atm).

The reaction product mixture weighed 143.9 g. The reactor methanolic wash weighed 163.9 g. GLPC showed the following materials to have been formed in the respective quantities shown:
M3P—not detected
M5MO3P—0.101 g. (0.69 mmoles)
M3MO4P—0.1583 g. (1.1 mmoles)
M24P—0.748 g. (6.68 mmoles)
DMH—5.47 g. (31.80 mmoles)

Total mmoles of product 40.27
M % selectivity to DMH:
$$\frac{31.80}{40.27} = 78.9\%$$

Conversion of BD:

-continued $$\frac{40.27 \text{ mmoles } BD\text{-derived products}}{10 \text{ g. } BD \text{ charged}/54} = \frac{40.27}{185.2} = 22\%$$

Butadiene accountability:
Butadiene feed: 10 g.
Utilized as carbonylated products:
0.0407 moles × 54 = 2.18 g. BD
Reactor methanolic wash, 163.9 g., contained 0.068% BD by GLPC, or 0.112 g. BD
Reaction product mixture, 143.9 g., contained 1.340% BD by GLPC, or 1.928 g. BD
Off-gas collector (30 psig, 34° C.) contained 0.071% BD, or, at standard temperature and pressure:

$$\frac{0.071 \times 28 \times 30 + 14.7}{14.7} \times \frac{273 + 25}{273 + 34} = 5.87 \text{ g. } BD$$

% accountability of $BD = \frac{0.112 + 1.928 + 2.18 + 5.87}{10} = 101\%$

EXAMPLES 3–8

These and subsequent examples were carried out in the manner described for Example 1, except where noted.

The materials charged to the reaction autoclave are listed in Table 1.

TABLE 2

| | Products from Examples 3–8 | | | |
|---|---|---|---|---|
| | Products, mmoles | | | |
| Ex. | Mono-carbonylated Products | DMH | % Conversion of BD | % Selectivity to DMH |
| 3 | 58.7 | 2.6 | 28 | 4 |
| 4 | 56.3 | 4.4 | 47 | 7 |
| 5 | 67.1 | 3.7 | 47 | 5 |
| 6 | 48.6 | 6.9 | 37 | 12 |
| 7 | 56.6 | 19.2 | 51 | 25 |
| 8 | 39.0 | 36.7 | 52 | 48 |

DMH: Dimethyl hex-3-enedioate
BD: Butadiene

Examples 3–8 show the effects on DMH selectivity of nitrile ligands (Examples 3–5), of metal halide ligands (examples 6 & 7) and the synergistic effect (example 8) of nitriles and metal halides. By "selectivity" is meant the molar percentage of the converted butadiene that appears as a particular product; in this case, DMH. Thus in example 8, 52% of the BD charged was converted to products and of these 48% was DMH, 52% was made up of other materials, essentially the monocarbonylated products.

TABLE 1

| | Autoclave charges for Examples 3–8 | | | | | | | | | | |
|---|---|---|---|---|---|---|---|---|---|---|---|
| | | | | | Charges, millimoles | | | | | | |
| Ex. | Cat. | mm | Quin. | mm | BD | CH₃OH | Solvent | mm | Additive | mm | H₂SO₄ |
| 3 | Pd(OAc)₂ | 2.7 | TPB | 80.1 | 150 | 320 | TL | 1458 | CH₃CN | 191 | 5.1 |
| 4 | " | " | " | " | 154 | 320 | " | " | SN | 140 | " |
| 5 | " | " | " | " | 150 | 320 | " | " | CH₃CN | 191 | " |
| 6 | " | " | " | " | 148 | 320 | " | " | LiI | 3.0 | " |
| 7 | " | " | " | " | 144 | 320 | " | " | CuCl₂ | 1.5 | " |
| 8 | " | " | " | " | 144 | 123 | PN | 1659 | DMK | 76.8 | " |
| | | | | | | | | | CuCl₂ | 29.8 | |

Reaction temperature 100° C., Pressure 121 atm - all examples
TPB: Tetrachloro-p-benzoquinone
BD: 1,3-butadiene
TL: Toluene
PN: Propionitrile
SN: Succinonitrile
DMK: 2,2-dimethoxypropane
Quin.: Quinone oxidant compound The monocarbonylated products and the desired dicarbonylated product, DMH, were quantified by GLPC as already described. Results are shown in Table 2.

EXAMPLES 9–16

These examples were carried out in the manner described for Example 1. Materials charged to the autoclave are listed in Table 3. Table 4 lists the products, BD conversions and selectivity to desired product.

TABLE 3

| | Autoclave charges for Examples 9–16 | | | | | | | | | | | |
|---|---|---|---|---|---|---|---|---|---|---|---|---|
| | | | | | Charges, millimoles | | | | | | | Temp |
| Ex. | Cat. | mm | Quin. | mm | BD | CH₃OH | Solvent | mm | Additive | mm | H₂SO₄ | °C. |
| 9 | PdCl₂ | 2.7 | PB | 79.6 | 172 | 123 | TL | 1166 | CH₃CN | 278 | 5.1 | 60–100 |
| 10 | " | 2.5 | 2EAQ | " | 152 | " | " | " | PN | 138 | " | 100 |
| 11 | " | " | " | " | 137 | " | CH₃CN | 2141 | DMK | 38 | " | " |
| 12 | " | " | DNQ | 77.6 | 165 | " | TL | 1166 | PN | 111 | " | " |
| 13 | " | " | DUQ | 78.0 | 148 | " | " | " | " | " | None | " |
| 14 | " | " | DDBQ | 82.2 | 128 | " | " | " | " | " | 5.1 | " |
| 15 | " | " | DPBQ | 73.3 | 165 | " | " | 1458 | CH₃CN | 191 | " | " |

TABLE 3-continued

Autoclave charges for Examples 9–16

| Ex. | Cat. | mm | Quin. | mm | BD | CH₃OH | Solvent | mm | Additive | mm | H₂SO₄ | Temp °C. |
|---|---|---|---|---|---|---|---|---|---|---|---|---|
| 16 | " | 2.7 | TPB | 80.1 | 144 | 320 | " | " | None | — | | " |

Reaction pressure was 121 atm for all examples
Cat.: Catalyst
Quin.: Quinone Oxidant Compound
BD: 1,3-butadiene
PB: p-benzoquinone
DDBQ: 2,3-dichloro-5,6-dicyano-p-benzoquinone
DPBQ: 2,5-diphenyl-p-benzoquinone
TPB: Tetrachloro-p-benzoquinone
DMK: 2,2-dimethoxypropane
PN: Propionitrile
TL: Toluene
DUQ: Duroquinone (tetramethyl-p-benzoquinone)
2EAQ: 2-ethylanthroquinone
DNQ: 2,3-dichloro-1,4-naphthoquinone

TABLE 4

Products from Examples 9–16

| Ex. | Mono-carbonylated Products (mmoles) | DMH (mmoles) | % Conversion of BD | % Selectivity to DMH |
|---|---|---|---|---|
| 9 | 61.1 | 4.2 | 38 | 7 |
| 10 | No reaction | | | |
| 11 | " | | | |
| 12 | 3.9 | 11.2 | 9 | 74 |
| 13 | 6.9 | 10.5 | 12 | 60 |
| 14 | Trace | n.d | — | — |
| 15 | 26.0 | 14.6 | 17 | 36 |
| 16 | 26.3 | 36.0 | 43 | 58 | n.d: Not detected
DMH: Dimethyl hex-3-enedioate
BD: Butadiene

These examples illustrate the use of a variety of quinone oxidant compounds. There was no reaction when 2-ethyl anthaquinone was used (ex. 10 and 11) and only a trace amount of product when 2,3-dichloro-5,6-dicyano-p-benzoquinone was used (ex. 14). All the other quinone oxidant compounds employed gave useful amounts of products, with tetrachloro-p-benzoquinone preferred, giving the largest yield (conversion × selectivity or 43% × 58% = 24.9%).

EXAMPLES 17–26

Materials charged to the autoclave are listed in Table 5. The amount (millimoles) of monocarbonylated products and dimethyl hex-3-enedioate (DMH) produced and BD conversion and DMH selectivity are shown in Table 6.

TABLE 5

Autoclave charges for Examples 17–26

| Ex. | Cat. | mm | Quin. | mm | BD | CH₃OH | Solvent | mm | Additive | mm | H₂SO₄ | Temp °C. |
|---|---|---|---|---|---|---|---|---|---|---|---|---|
| 17 | PdCl₂ | 2.5 | TBP | 80.1 | 165 | 123 | TL | 1166 | PN | 138 | 5.1 | 60 |
| 18 | " | 2.4 | " | " | 144 | " | " | " | " | " | " | 125 |
| 19 | " | 2.7 | " | " | 146 | " | " | 1458 | Acetic acid | 25.2 | None | 100 |
| 20 | " | 2.5 | TPB | 80.1 | 130 | 135ᵃ | CY | 1458 | PN | 138 | 5.1 | " |
| 21 | " | 2.7 | " | " | 144 | 320 | TL | " | None | — | " | " |
| 22 | " | " | " | " | 152 | " | " | " | " | — | None | " |
| 23 | " | " | " | " | 167 | " | " | " | " | — | 5.1 | " |
| 24 | " | " | " | " | 157 | " | " | " | " | — | None | " |
| 25 | " | " | " | " | 148 | 257ᵇ | " | " | PN | 138 | 5.1 | " |
| 26 | " | " | " | " | " | 320 | " | " | " | " | " | " |

Reaction pressure for Example 18 was 34 atm - all other examples: 121 atm
ᵃmillimoles n-butanol
Quin.: Quinone Oxidant Compound
BD: 1,3-butadiene
TL: Toluene
CY: Cyclohexane
Cat.: Catalyst
TPB: Tetrachloro-p-benzoquinone
ᵇmillimoles ethanol
PN: Propionitrile

TABLE 6

Products from Examples 17–26

| Ex. | Mono-carbonylated Products (mmoles) | DMH (mmoles) | % Conversion of BD | % Selectivity to DMH |
|---|---|---|---|---|
| 17 | 7.3 | 17.8 | 15 | 71 |
| 18 | 44.6 | 4.2 | 34 | 9 |
| 19 | 13.0 | 29.9 | 29 | 70 |
| 20 | 44.1 | 57.4 | 69 | 57ᵃ |
| 21 | 26.3 | 36.0 | 43 | 58 |
| 22 | 36.5 | 45.3 | 54 | 55 |
| 23 | 28.9 | 40.1 | 41 | 58 |
| 24 | 33.7 | 36.4 | 45 | 52 |
| 25 | 37.7 | 47.2 | 57 | 56ᵇ |
| 26 | 25.7 | 21.2 | 32 | 45 |

DMH: Dimethyl hex-3-enedioate
BD: Butadiene
ᵃdibutyl hex-3-enedioate
ᵇdiethyl hex-3-enedioate Example 17 shows that excellent selectivities to the desired DMH product can be obtained even at temperatures as low as 60° C. Example 18 shows that the reaction proceeds at 125° C. at pressures as low as 500 psig, though DMH selectivity is relatively low. Example 19 omitted the sulfuric acid added in run 17, but included acetic acid along with the propionitrile additive. Selectivity to DMH was excellent (70%). No propionitrile was employed in Examples 21–24, with examples 21 and 23 using a small added amount of sulfuric acid, examples 22 and 24 using no sulfuric acid. In all cases selectivity to DMH was greater than 50%. Example 20 shows that n-butanol can be used in place of the methanol employed in most cases, without significantly affecting the types of products made. Similarly, ethanol is employed in Example 25, and the reaction proceeded in a manner similar to that of other examples.

EXAMPLES 27–29

Charged to the autoclave consisted of butadiene, methanol, toluene, propionitrile, sulfuric acid, tetrachloro-p-benzoquinone and palladium chloride in the amounts shown in Table 7. Examples 27 and 29 were in essence duplicates, while in Example 28 a 4-fold excess of methanol was employed. The examples were run in the manner already described. Table 8 lists the product data and shows that runs 27 and 29 gave essentially the same product distribution. Conversions and selectivities for example 28 were very little different, though the presence of small amounts of dimethyl oxalate was observed on the gas chromatogram. Dimethyl oxalate could arise from reaction of carbon monoxide and methanol under oxidizing conditions.

TABLE 8

| | Products from Examples 27-29 | | | |
|---|---|---|---|---|
| | Products, mmoles | | | |
| Ex. | Mono-carbonylated Products | DMH | % Conversion of BD | % Selectivity to DMH |
| 27 | 27.2 | 34.3 | 35 | 56 |
| 28 | 18.0 | 19.3 | 30 | 52 |
| 29 | 20.9 | 34.0 | 38 | 62 |

BD: 1,3-butadiene
DMH: Dimethyl hex-3-enedioate

EXAMPLES 30–40

These examples show butadiene carbonylation in the presence of a variety of nitriles, which serve as cosolvents and as ligands for the platinum-group metal catalyst (in these examples, palladium). The experiments were carried out as described in Example 1, at 100° C. and 1800 psig (121 atm) reactor pressure.

Autoclave charges are shown in Table 9. Product data are shown in Table 10. Examples 37–40 used very similar charges. Example 37, 38 and 39 used 138 mmoles propionitrile as cosolvent and ligand; no nitrile was used in Ex. 40. Examples 37, 38 and 40 contained 5.1 mmoles concentrated sulfuric acid to the autoclave charge; no concentrated acid was used in example 39. Example 37, additionally, used 130 mmoles of 2,2-dimethoxypropane (the dimethyl ketal of acetone) as a dehydrating agent. The close similarity of the butadiene conversion data and selectivity to dimethyl hex-3-ene-

TABLE 7

| Autoclave charges for Examples 27-29 | | | | | | | | | |
|---|---|---|---|---|---|---|---|---|---|
| | | | | | Charges, millimoles | | | | |
| Ex. | Cat. | mm | Quin. | mm | BD | CH₃OH | Toluene | PN | H₂SO₄ |
| 27 | PdCl₂ | 2.85 | TPB | 80.1 | 175 | 123 | 583 | 829 | 5.1 |
| 28 | " | 2.8 | " | " | 144 | 615 | " | " | " |
| 29 | " | 2.5 | " | " | " | 123 | " | " | " |

Reaction temperature for all Examples: 100° C.; Reaction Pressure 121 atm
TPB: Tetrachloro-p-benzoquinone
BD: 1,3-butadiene
PN: Propionitrile dioate in these 4 examples (Table 10) shows that the presence or absence of dehydrating agents, concentrated sulfuric acid or nitriles does not greatly affect conversion or selectivity. Charges in all examples in table 9 contained 80.1 millimoles of tetrachloro-p-benzoquinone internal oxidant.

TABLE 9

| Autoclave charges for Examples 30-40 | | | | | | | | |
|---|---|---|---|---|---|---|---|---|
| | | | | Charges, millimoles | | | | |
| Ex. | Cat. | mm | BD | Toluene | CH₃OH | H₂SO₄ | Added Component(s) | mm |
| 30 | PdCl₂ | 2.3 | 167 | 166 | 123 | 5.1 | PN | 138 |
| 31 | " | 2.9 | 154 | " | " | " | BDN | 88 |
| 32 | " | 2.4 | 141 | " | " | " | ACN | 136 |
| 33 | " | 2.5 | " | " | " | " | BN | 139 |
| 34 | " | 2.5 | 165 | " | " | " | SN | 140 |
| 35 | " | 2.4 | " | " | " | None | PN | 138 |
| 36 | " | 2.5 | 141 | " | " | 5.1 | MACN | 140 |
| 37 | " | 2.5 | 146 | " | " | " | PN | 138 |
| | | | | | | | DMK | 130 |
| 38 | " | 2.6 | " | " | " | " | PN | 138 |
| 39 | " | 2.7 | 167 | 1458 | 320 | None | " | " |

TABLE 9-continued

Autoclave charges for Examples 30–40

Charges, millimoles

| Ex. | Cat. | mm | BD | Toluene | CH$_3$OH | H$_2$SO$_4$ | Added Component(s) | mm |
|---|---|---|---|---|---|---|---|---|
| 40 | " | " | 144 | " | " | 5.1 | None | — |

BD: 1,3-butadiene
BDN: Phthalonitrile
ACN: Acetonitrile
BN: Benzonitrile
SN: Succinonitrile
MACN: Methoxyacetonitrile
DMK: 2,2-dimethoxypropane

TABLE 10

Products from Examples 30–40

| Ex. | Mono-carbonylated Products (mmoles) | DMH (mmoles) | % Conversion of BD | % Selectivity to DMH |
|---|---|---|---|---|
| 30 | 15.0 | 29.0 | 26 | 67 |
| 31 | 35.4 | 31.8 | 47 | 44 |
| 32 | 17.0 | 34.7 | 37 | 67 |
| 33 | 35.7 | 25.2 | 43 | 41 |
| 34 | 17.4 | 28.6 | 28 | 62 |
| 35 | 20.1 | 32.5 | 32 | 62 |
| 36 | 25.1 | 26.2 | 36 | 54 |
| 37 | 22.1 | 36.7 | 40 | 62 |
| 38 | 18.0 | 33.6 | 35 | 66 |
| 39 | 27.5 | 38.5 | 40 | 58 |
| 40 | 26.3 | 36.0 | 43 | 58 |

BD: 1,3-butadiene
DMH: dimethyl hex-3-enedioate

EXAMPLES 41–48

Examples 41–48 show the use of triphenyl phosphine or substituted triphenyl phosphine ligands on palladium chloride as catalyst. In all cases the autoclave charge contained 80.1 millimoles of tetrachloro-p-benzoquinone as internal oxidant to maintain palladium is its desirable doubly charged cationic form. The conditions used were as described in Example 1, except that Example 48 was carried out at 90° C. and a pressure of 1800 psig (121 atmospheres). All examples used 1166 millimoles of toluene as solvent. In the case of Example 45, an additional 14.4 millimoles of triphenyl phosphine was added to the solvent. In Table 11 and later tables, the symbol $\phi$ is used to indicate the phenyl group. Product data are shown in Table 12.

TABLE 11

Autoclave charges for Examples 41–48

Charges, millimoles

| Ex. | Cat. | mm | BD | CH$_3$OH | H$_2$SO$_4$ | Added Component(s) | mm |
|---|---|---|---|---|---|---|---|
| 41 | PdA | 2.4 | 154 | 123 | 5.1 | None | — |
| 42 | " | 2.2 | 185 | " | " | " | — |
| 43 | " | 2.4 | 130 | " | " | " | — |
| 44 | " | " | 141 | " | None | " | — |
| 45 | " | " | 169 | " | 5.1 | Triphenyl phosphine | 14.4 |
| 46 | PdB | 2.7 | 152 | " | " | None | — |
| 47 | PdC | 2.5 | 146 | " | " | " | — |
| 48$^a$ | PdA | 2.4 | 139 | " | " | " | — |

$^a$run at 90° C.
BD: 1,3-butadiene
PdA: Cl$_2$($\phi_3$P)$_2$ Pd, dichlorobistriphenylphosphine
PdB: Cl$_2$([p-CH$_3$O—$\phi$]$_3$P)$_2$Pd, dichloro-bis(tris-p-methoxyphenyl)phosphine palladium II
PdC: Cl$_2$([p-F—$\phi$]$_3$P)$_2$Pd, dichlorobis(tri-p-fluorophenyl)phosphine palladium II

TABLE 12

Products from Examples 41–48

| Ex. | Mono-carbonylated Products (mmoles) | DMH (mmoles) | % Conversion of BD | % Selectivity to DMH |
|---|---|---|---|---|
| 41 | 9.7 | 31.0 | 28 | 76 |
| 42 | 8.5 | 32.0 | 22 | 79 |
| 43 | 10.3 | 37.7 | 38 | 79 |
| 44 | 13.3 | 32.8 | 33 | 71 |
| 45 | 1.0 | 4.4 | 4 | 74 |
| 46 | 16.7 | 30.4 | 31 | 64 |
| 47 | 5.4 | 12.7 | 12 | 70 |
| 48 | 7.5 | 30.6 | 28 | 80 |

When an excess of triphenyl phosphine was used (Ex. 45), conversion of butadiene was low in the time alloted for the experiment; that is, the reaction was slow. Similarly, Ex. 47, using tri(p-fluorophenyl)phosphine as the ligand was a slow reaction. Selectivities to desired product were high in all cases.

EXAMPLES 49–56

These runs were carried out as in Example 1, at 100° C. and 1800 psig, but using added lithium iodide or tetrabutylammonium iodide, as shown in Table 13. In all cases, the primary solvent was toluene, 1458 millimoles (1166 mmoles in Ex. 53).

TABLE 13

Autoclave charges for Examples 49–56

Charges, millimoles

| Ex. | Cat. | mm | BD | CH$_3$OH | TPB | H$_2$SO$_4$ | Iodide | mm |
|---|---|---|---|---|---|---|---|---|
| 49 | Cl$_2$($\phi_3$P)$_2$Pd | 2.4 | 154 | 123 | 80.1 | 5.1 | LiI | 15.0 |
| 50 | " | " | 165 | " | " | " | Bu$_4$NI | 2.7 |
| 51 | " | " | 135 | 369 | " | " | LiI | 3.0 |
| 52 | " | " | 146 | 320 | " | " | " | 3.3 |
| 53 | " | " | 150 | 246 | " | " | " | " |
| 54 | " | 1.2 | 152 | 369 | " | " | " | 1.5 |
| 55 | " | 2.4 | " | " | 59.0 | " | " | 3.1 |

TABLE 13-continued

| | Autoclave charges for Examples 49-56 | | | | | | | |
|---|---|---|---|---|---|---|---|---|
| | | | Charges, millimoles | | | | | |
| Ex. | Cat. | mm | BD | CH$_3$OH | TPB | H$_2$SO$_4$ | Iodide | mm |
| 56 | " | " | 139 | 320 | 80.1 | none | " | " |

BD: Butadiene
TPB: Tetrachloro-p-benzoquinone

Addition of the lithium iodide or tetrabutyl ammonium iodide salts appeared to increase the butadiene conversion, and in most cases selectivity to DMH was excellent, so that overall yield of DMH (selectivity times conversion of butadiene) was excellent. Product data are shown in Table 14.

TABLE 14

| | Products from Examples 49-56 | | | |
|---|---|---|---|---|
| | Products, mmoles | | | |
| Ex. | Mono-carbonylated Products | DMH | % Conversion of BD | % Selectivity to DMH |
| 49 | a | a | — | — |
| 50 | 25.2 | 36.9 | 38 | 60 |
| 51 | 17.0 | 36.4 | 40 | 68 |
| 52 | 19.6 | 47.2 | 46 | 71 |
| 53 | 19.2 | 45.9 | 43 | " |
| 54 | 19.7 | 44.3 | 42 | 69 |
| 55 | 14.9 | 28.8 | 29 | 66 |
| 56 | 42.2 | 28.1 | 51 | 40 | a: no product
DMH: dimethyl hex-3-enedioate
BD: butadiene

No products were formed in Example 49, due, it is presumed, to an excessive level of iodide.

EXAMPLES 57-64

These Examples illustrate the use of palladium compounds other than palladium chloride with or without ligands, and other platinum-group metal compounds (the iodides of ruthenium, rhodium and platinum). All experiments (see Table 15) used 1458 millimoles of toluene as solvent and were run at 100° C. and 1800 psig pressure.

TABLE 15

| | Autoclave charges for Examples 57-64 | | | | | | | |
|---|---|---|---|---|---|---|---|---|
| | | | | Charges, millimoles | | | | |
| Ex. | Cat. | mm | BD | TPB | CH$_3$OH | H$_2$SO$_4$ | Added Component(s) | mm |
| 57 | PdSO$_4$ | 2.3 | 170 | 80.1 | 123 | none | PN | 138 |
| 58 | Pd black | 2.5$^a$ | 159 | 610 | " | 5.1 | " | " |
| 59 | " | " | 139 | " | " | none | " | " |
| | | | | | | | Bu$_4$NI | 2.7 |
| 60 | PdBr$_2$ | 2.3 | 156 | 80.1 | 320 | " | none | — |
| 61 | PdI$_2$ | 2.0 | 154 | " | " | " | " | — |
| 62 | RuI$_3$ | 2.1 | " | " | " | " | LiI | 2.8 |
| 63 | RhI$_3$ | 2.2 | 148 | " | " | " | " | 2.3 |
| 64 | PtI$_3$ | 2.3 | " | " | " | " | " | " |

$^a$Palladium black, in milligram atoms
PN: Propionitrile

Product data are presented in Table 16.

TABLE 16

| | Products from Examples 57-64 | | | |
|---|---|---|---|---|
| | Products, mmoles | | | |
| Ex. | Mono-carbonylated Products | DMH | % Conversion of BD | % Selectivity to DMH |
| 57 | 35.0 | 16.2 | 30 | 32 |
| 58 | 20.3 | 5.8 | 16 | 22 |
| 59 | 17.1 | 21.4 | 26 | 56 |

TABLE 16-continued

| | Products from Examples 57-64 | | | |
|---|---|---|---|---|
| | Products, mmoles | | | |
| Ex. | Mono-carbonylated Products | DMH | % Conversion of BD | % Selectivity to DMH |
| 60 | 22.9 | 54.7 | 50 | 71 |
| 61 | 57.5 | 8.7 | 43 | 13 |
| 62 | 2.7 | 2.6 | 3 | 49 |
| 63 | 2.3 | 1.2 | 2 | 35 |
| 64 | Trace | Trace | — | — |

We claim:

1. A process for the preparation of dimethyl adipate comprising reacting 1,3-butadiene with carbon monoxide under reactive conditions of temperature and pressure in the presence of methanol, a catalyst comprising a platinum metal group compound in a high oxidation state, and a quinone oxidant to form an intermediate comprising dimethyl hex-3-enedioate, and hydrogenating the dimethyl hex-3-enedioate to form dimethyl adipate.

2. The process of claim 1 wherein the methanol is present in the amount of 0.7-3.5 mole equivalents based on the conjugated diene.

3. The process of claim 1 conducted in the presence of a small amount of a dehydrating agent.

4. The process of claim 1 wherein the platinum-group elements in the catalyst are selected from the grop consisting of ruthenium, rhodium, palladium, osmium, iridium, platinum, and mixtures thereof.

5. The process of claim 1 wherein the platinum-group element is palladium.

6. The process of claim 1 wherein the catalyst is selected from the group consisting of ruthenium trichloride, rhodium tribromide, palladium iodide, palladium chloride, osmium sulfate, iridium nitrate, platinum chloride, and mixtures thereof.

7. The process of claim 1 conducted in the presence of a ligand.

8. The process of claim 1 wherein the catalyst is homogeneous.

9. The process of claim 8 wherein the process is conducted in the pressure of a ligand and the catalyst and the ligand are formed into a complex in situ.

10. The process of claim 8 wherein the process is conducted in the process of a ligand and the ligand and the catalyst are formed into a complex before introduction into the reaction.

11. The process of claim 9 wherein the ligand is selected from the group consisting of triphenyl phosphine, tris(p-methoxphenyl)phosphine, tris(p-fluorophenyl)phosphine, tributyl phosphine, triphenyl arsine, triethyl arsine, triphenyl stibine, benzonitrile, acetonitrile, propionitrile, valeronitrile, succinonitrile, glutaronitrile, triphenyl phosphite, lithium chloride, sodium bromide, lithium iodide, potassium iodide and copper chloride.

12. The process of claim 1 wherein the catalyst is heterogeneous.

13. The process of claim 1 conducted in a solvent selected from the group consisting of benzene, toluene, xylene, cyclohexane, cyclopentane, cyclooctane, n-hexane, iso-octane, 2,5-dimethylheptane, acetonitrile, propionitrile, benzonitrile, cyclohexanone, acetone, acetophenone, 2-butanone, 1,2-dimethoxyethane, 3,6,9-trioxaundecane, 2,5,8-trioxanonane, 2,2-diethoxypropane, 1,1-dimethoxycyclohexane, ethyl acetate, methyl propionate, butyl propionate, methyl benzoate, dimethyl adipate, and mixtures thereof.

14. The process of claim 1 conducted in the presence of small amounts of an acid selected from the group consisting of acetic acid, trifluoroacetic acid, sulfuric acid, hydrochloric acid, hydroiodic acid, and mixtures thereof.

15. The process of claim 1 wherein the quinone oxidant is selected from the group consisting of 1,4-benzoquinone, 2,5-dichloro-1,4-benzoquinone, tetrachloro-1,4-benzoquinone (p-chloranil), 2,3-dicyano-1,4-benzoquinone, 2,3-dichloro-1,4-naphthoquinone, tetramethyl-1,4-benzoquinone, 2,3-dichloro-5,6-dicyano-1,4-benzoquinone, 2,5-diphenyl-1,4-benzoquinone, 2,3-dimethyl-1,4-naphthoquinone, 1,4-naphthoquinone, and mixtures thereof.

16. The process of claim 1 conducted at a pressure of 34–350 atmospheres.

17. The process of claim 1 conducted at a temperature of 60°–190° C.

18. A process for the preparation of dimethyl adipate from 1,3-butadiene comprising reacting the 1,3-butadiene in a solvent selected from the group consisting of benzene, toluene, xylene, cyclohexane, cyclopentane, cyclooctane, n-hexane, iso-octane, 2,5-dimethylheptane, acetonitrile, propionitrile, benzonitrile, cyclohexanone, acetone, acetophenone, 2-butanone, 1,2-dimethoxyethane, 3,6,9-trioxaundecane, 2,5,8-trioxanonane, 2,2-diethoxypropane, 1,1-dimethoxycyclohexane, ethyl acetate, methyl propionate, butyl propionate, methyl benzoate, dimethyl adipate, and mixtures thereof, with carbon monoxide under reactive conditions of temperature and pressure in the presence of methanol, a ligand selected from the group consisting of triphenyl phosphine, tris(p-methoxyphenyl)phosphine, tris(p-chlorophenyl)phosphine, tributyl phosphine, triphenyl arsine, triethyl arsine, triphenyl stibine, benzonitrile, acetonitrile, propionitrile, valeronitrile, succinonitrile, glutaronitrile, triphenyl phosphite, lithium chloride, sodium bromide, lithium iodide, potassium iodide and copper chloride, a catalyst comprising a platinum group metal compound in a high oxidation state and a quinone oxidant, thereby to form an intermediate comprising dimethyl hex-3-enedioate, catalytically and hydrogenating the dimethyl hex-3-enedioate thereby to form dimethyl adipate.

19. The process of claim 18 wherein the oxidant is p-chloranil.

* * * * *